(12) United States Patent
Osawa et al.

(10) Patent No.: US 11,035,748 B2
(45) Date of Patent: Jun. 15, 2021

(54) PRESSURE SENSOR ATTACHMENT STRUCTURE

(71) Applicant: Nidec Tosok Corporation, Zama (JP)

(72) Inventors: Tomoka Osawa, Zama (JP); Hironobu Wakabayashi, Zama (JP); Toshiaki Nakamura, Zama (JP); Hiroshi Tatsuta, Zama (JP)

(73) Assignee: NIDEC TOSOK CORPORATION, Kanagawa (JP)

( * ) Notice: Subject to any disclaimer, the term of this patent is extended or adjusted under 35 U.S.C. 154(b) by 73 days.

(21) Appl. No.: 16/569,839

(22) Filed: Sep. 13, 2019

(65) Prior Publication Data

US 2020/0003656 A1 Jan. 2, 2020

Related U.S. Application Data

(62) Division of application No. 15/666,748, filed on Aug. 2, 2017, now Pat. No. 10,591,378.

(30) Foreign Application Priority Data

Aug. 3, 2016 (JP) ................................. 2016-153214

(51) Int. Cl.
*G01L 19/14* (2006.01)
*G01L 19/00* (2006.01)
(Continued)

(52) U.S. Cl.
CPC ............ *G01L 19/147* (2013.01); *F16K 27/00* (2013.01); *G01L 19/003* (2013.01);
(Continued)

(58) Field of Classification Search
CPC ......... G01L 19/142–144; G01L 19/147; G01L 19/0645; G01L 19/0046; F16H 61/0009;
(Continued)

(56) References Cited

U.S. PATENT DOCUMENTS 4,574,811 A * 3/1986 Stephens .................. G01L 19/14
600/488
2001/0018380 A1 8/2001 Fritzsche et al.
(Continued)

FOREIGN PATENT DOCUMENTS

JP 05-198206 A 8/1993
JP 2002-523699 A 7/2002
(Continued)

OTHER PUBLICATIONS

Osawa et al., "Sensor attachment Structure", U.S. Appl. No. 15/666,748, filed Aug. 2, 2017.
(Continued)

*Primary Examiner* — David L Singer
(74) *Attorney, Agent, or Firm* — Keating & Bennett

(57) ABSTRACT

A sensor attachment structure of an oil pressure sensor suitable for use as a control valve of an automobile transmission includes a sensor case inserted into an accommodation space 4 of a valve upper-body portion such that a body portion of the sensor case is capable of rotating about a vertical central axis. A stopper projects in a horizontal direction from the upper body, the stopper being movable vertically in a guide groove of the sensor case, and a rotatable relative to a restricting portion of the central case to restrict a vertical movement of the stopper to prevent the oil pressure sensor from falling off the upper body.

3 Claims, 6 Drawing Sheets

(51) Int. Cl.
*F16K 27/00* (2006.01)
*G01M 13/02* (2019.01)
*F16H 61/02* (2006.01)
*F16H 61/00* (2006.01)

(52) U.S. Cl.
CPC ........... *G01L 19/142* (2013.01); *G01M 13/02* (2013.01); *F16H 61/0021* (2013.01); *F16H 61/0251* (2013.01)

(58) Field of Classification Search
CPC .... F16H 61/0206; F15B 13/086; F16K 27/00; G01D 11/245
USPC .................................. 73/715–731, 756, 706
See application file for complete search history.

(56) References Cited

U.S. PATENT DOCUMENTS

| | | | | |
|---|---|---|---|---|
| 2002/0189335 A1* | 12/2002 | Matsumura | ......... | G01L 19/0007 73/114.38 |
| 2005/0032402 A1* | 2/2005 | Takanashi | ........... | G01L 19/0061 439/76.2 |
| 2005/0193809 A1* | 9/2005 | Matsumura | ......... | G01L 19/0007 73/114.38 |
| 2006/0213276 A1* | 9/2006 | Ueyanagi | ............ | G01L 19/0627 73/754 |
| 2009/0120196 A1* | 5/2009 | Eckhardt | ............. | G01L 19/0007 73/756 |
| 2011/0088480 A1* | 4/2011 | Koehler | ............ | G01L 19/0084 73/753 |
| 2011/0138924 A1* | 6/2011 | Colombo | ............ | G01L 19/0038 73/756 |
| 2012/0118086 A1* | 5/2012 | Horn | ................... | G01D 11/245 73/866.5 |
| 2013/0056100 A1* | 3/2013 | Imaizumi | .............. | B60T 13/662 137/560 |
| 2016/0076960 A1 | 3/2016 | Sato et al. | | |
| 2016/0091377 A1* | 3/2016 | Tohyama | ............. | G01L 9/0055 73/720 |
| 2017/0314700 A1 | 11/2017 | Iwanaga et al. | | |

FOREIGN PATENT DOCUMENTS

| | | |
|---|---|---|
| JP | 2016-061661 A | 4/2016 |
| WO | 2016/076188 A1 | 5/2016 |

OTHER PUBLICATIONS

Official Communication issued in corresponding Japanese Patent Application No. 2016-153214, dated Jul. 14, 2020.

* cited by examiner

PRESSURE SENSOR ATTACHMENT STRUCTURE

CROSS REFERENCE TO RELATED APPLICATIONS

This application claims the benefit of priority to Japanese Patent Application No. 2016-153214 filed on Aug. 3, 2016. The entire contents of this application are hereby incorporated herein by reference.

BACKGROUND OF THE INVENTION

1. Field of the Invention

The present invention relates to a sensor attachment structure that is suitable for use in, for example, a control valve of an automobile transmission.

2. Description of the Related Art

Automatic transmissions of vehicles include a control valve for controlling a transmission mechanism. The control valve controls the transmission mechanism by supplying or stopping supplying a predetermined oil pressure to the transmission mechanism by using a solenoid valve. Some existing control valves include a valve body in which an upper body is superposed on a lower body. An oil passage, in which hydraulic oil flows, is formed in the valve body. A solenoid valve for switching oil pressure and a sensor for detecting oil pressure in the oil passage are disposed in the valve body.

In most existing control valves, electronic devices, such as a sensor, are independently attached onto the valve body. As reduction in size has been needed in recent years, for example, control valves are required to have a built-in structure illustrated in FIG. 8, in which an oil pressure sensor 3 is held between an upper body 1 and a lower body 2.

For example, such a structure is described in Japanese Unexamined Patent Application Publication No. 2010-174991, Domestic Re-publication of PCT International Publication for Patent Application No. 2010/058800, and Japanese Unexamined Patent Application Publication No. 2011-134801.

FIG. 9 illustrates a method used in existing technologies to hold the oil pressure sensor 3 between the upper body 1 and the lower body 2. In this method, first, the upper body 1 is turned upside down so that a lower surface thereof faces upward, the oil pressure sensor 3 is turned upside down, and the oil pressure sensor 3 is inserted into an accommodation space 4 in the upper body 1. Next, in a state in which the oil pressure sensor 3 is fitted into the accommodation space 4, the upper body 1 is turned right side up and superposed on the lower body 2, and the upper body 1 and the lower body 2 are fixed to each other.

If the oil pressure sensor 3 is first placed on the lower body 2 and then the upper body 1 is superposed on the lower body 2, the oil pressure sensor 3 and the accommodation space 4 are hidden by the upper body 1, it is difficult to adjust the positions of the oil pressure sensor 3 and the accommodation space 4 relative to each other, and it is difficult to insert the oil pressure sensor 3 into the accommodation space 4. Therefore, as described above, the oil pressure sensor 3 is attached to the upper body 1 in a state in which the upper body 1 is turned upside down.

However, with such a method, after the oil pressure sensor 3 has been attached and when the upper body 1 is turned right side up to be superposed on the lower body 2, the oil pressure sensor 3, which has been fitted into the accommodation space 4, may fall due to its own weight. Therefore, an operator needs to superpose the upper body 1 on the lower body 2 to adjust the positions of the upper body 1 and the lower body relative to each other while pressing the oil pressure sensor 3 so that the oil pressure sensor 3 may not fall. Thus, this method has a problem of very low workability. Moreover, there is a probability that the oil pressure sensor 3 becomes damaged, because an operator cannot avoid fall of the oil pressure sensor 3 from the upper body 1 even when the operator pays attention.

The present invention has been conceived to provide a sensor attachment structure which prevents an oil pressure sensor from falling from an upper body even when the upper body is turned upside down, and which allows installation of the oil pressure sensor and positioning of the upper body and a lower body to be accomplished by simple operations.

SUMMARY OF THE INVENTION

A sensor attachment structure according to a preferred embodiment of the present invention includes an oil pressure sensor including a sensor case and a pressure sensor element accommodated in the sensor case, the sensor case including a body portion having a circular horizontal section; and a valve body including an upper body and a lower body, the upper body including an accommodation space having a wall surface having a circular horizontal section, the accommodation space having the body portion inserted therein such that the body portion is capable of rotating about a central axis thereof extending in a vertical direction, the lower body including an oil passage arranged to extend therethrough toward the upper body. The sensor case includes a stopper arranged to project in a horizontal direction in an outer circumferential surface of the body portion. The accommodation space includes a guide groove arranged to extend in the vertical direction at the wall surface thereof, the guide groove being arranged to allow the stopper to move therein. The upper body includes a restricting portion arranged to restrict a vertical movement of the stopper in a situation in which the body portion is disposed in the accommodation space. A space portion allowing the stopper to move therein is arranged between the guide groove and the restricting portion.

The sensor attachment structure according to the above preferred embodiment of the present invention preferably has the following features: the accommodation space is a through hole defined in the upper body; the restricting portion is a portion of an upper edge of the through hole, the portion including no portion of the guide groove; and the space portion is a space adjoining the upper edge of the through hole and connected to an upper portion of the guide groove.

A sensor attachment structure according to another preferred embodiment of the present invention includes an oil pressure sensor including a sensor case and a pressure sensor element accommodated in the sensor case, the sensor case including a body portion having a circular horizontal section; and a valve body including an upper body and a lower body, the upper body including an accommodation space having a wall surface having a circular horizontal section, the accommodation space having the body portion inserted therein such that the body portion is capable of rotating about a central axis thereof extending in a vertical direction, the lower body including an oil passage arranged to extend therethrough toward the upper body. The sensor case includes a stopper arranged to project in a horizontal direction toward an interior of the accommodation space at the wall surface of the accommodation space. An outer circumferential surface of the body portion includes a guide groove arranged to extend in the vertical direction and allow the stopper to move therein. The outer circumferential surface of the body portion includes a restricting portion arranged to restrict a vertical movement of the stopper in a situation in which the body portion has been inserted in the accommodation space. A space portion allowing the stopper to move therein is arranged between the guide groove and the restricting portion.

The sensor attachment structure according to the other preferred embodiment of the present invention preferably has the following features: the space portion is a horizontal groove arranged to extend in a circumferential direction at the outer circumferential surface of the body portion, the horizontal groove being connected to the guide groove extending in the vertical direction; and the restricting portion is defined by a lower edge of the horizontal groove.

The sensor attachment structure according to each of the above preferred embodiments of the present invention may additionally have the following features: the sensor case includes a lower case and an upper case fixed above the lower case; the upper case is made of a resin, and is arranged to have the pressure sensor element disposed inside thereof; and the lower case is made of a metal, has arranged inside thereof an oil introducing space connected to the oil passage defined in the lower body, includes a collar portion at an outer circumference thereof, and is held with the collar portion being held between the upper body and the lower body.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 8:
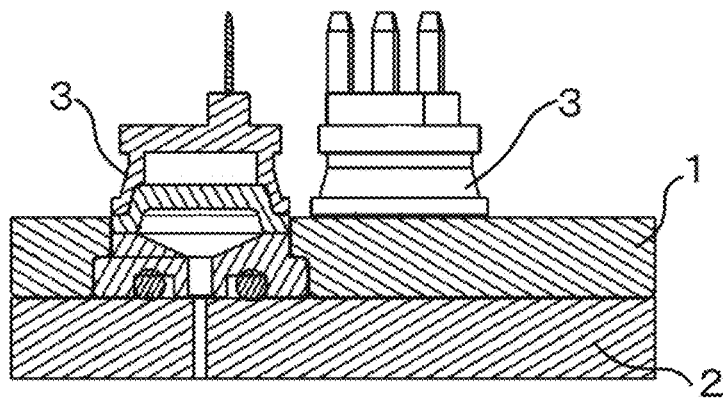
FIG. 8 is a vertical sectional view illustrating a situation in which an oil pressure sensor is attached to a valve body.
Figure 9:
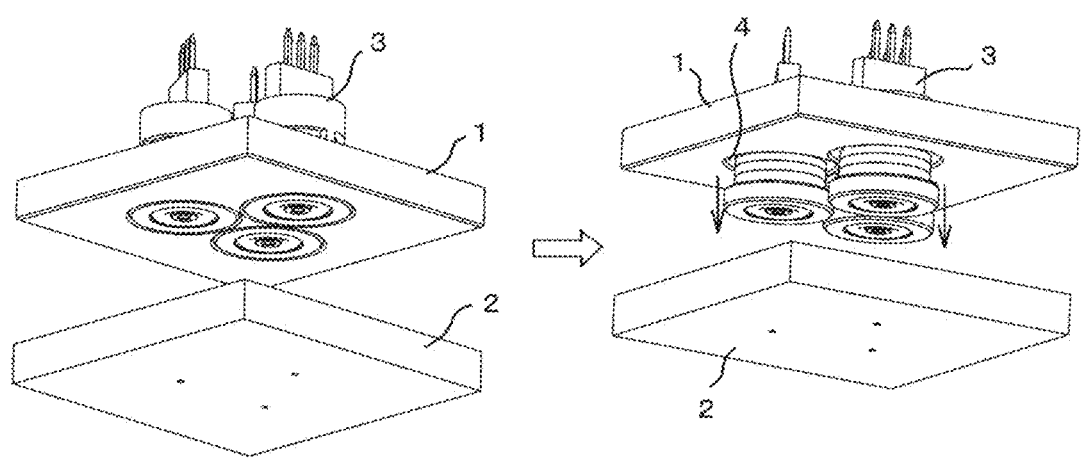
FIG. 9 is a perspective view illustrating how oil pressure sensors fall from a valve body.

Hereinafter, preferred embodiments of the present invention will be described. In the figures for each preferred embodiment, members or portions that have their equivalents in a related-art structure illustrated in FIGS. 8 and 9 are denoted by the same reference numerals as those of their equivalents in the related-art structure, and redundant descriptions of such members and portions will be omitted. In a description of each preferred embodiment, the term "vertical direction" refers to a direction in which an upper body and a lower body are placed one upon the other, and the term "axis" refers to a central axis of an oil pressure sensor extending in the vertical direction. In addition, an inner side and an outer side are defined with reference to the central axis of the oil pressure sensor, and the terms "circumferential direction" and "axial direction" refer to a circumferential direction about the central axis and an axial direction of the central axis, respectively, unless otherwise noted.

1. First Preferred Embodiment 1.1 Structure

Figure 1:
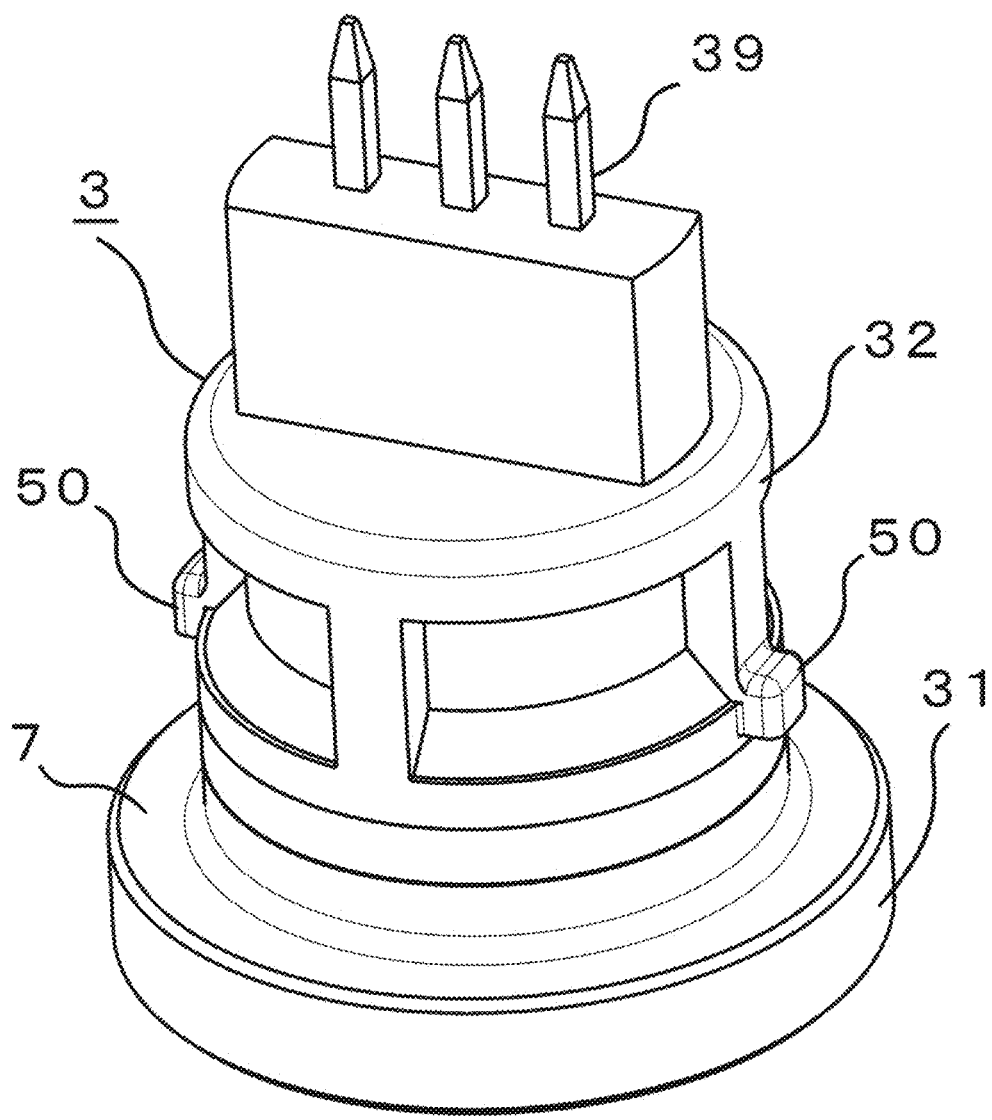
FIG. 1 is a perspective view of a first preferred embodiment of the present invention.
Figure 2:
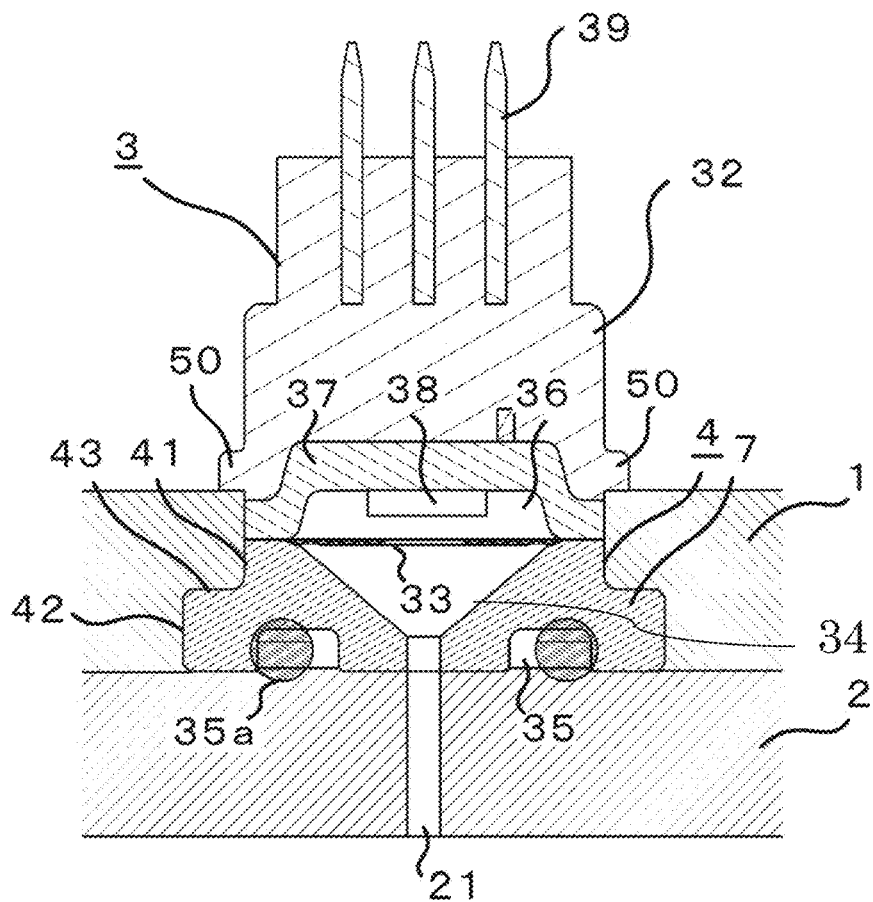
FIG. 2 is a vertical sectional view of the first preferred embodiment.

A first preferred embodiment of the present invention will now be described below with reference to FIGS. 1, 2, and 3. In the first preferred embodiment, stoppers are included in a sensor case, while restricting portions are included in an upper body.

A valve body includes an upper body 1 and a lower body 2. The upper body 1 includes an accommodation space 4 in which a portion of an oil pressure sensor 3 is accommodated. The lower body 2 includes an oil passage 21 arranged to extend therethrough and upward toward the upper body 1, and the oil pressure sensor 3 is fixed at an opening portion of the oil passage 21.

The accommodation space 4 is a through hole arranged to pass through the upper body 1 from an upper surface to a lower surface of the upper body 1. A case of the oil pressure sensor 3 is inserted upwardly through the accommodation space 4 along a central axis thereof. An upper edge of the through hole, which defines the accommodation space 4, in the upper surface of the upper body 1 defines restricting portions 52 arranged to prevent stoppers 50, which are included in an upper case 32, from moving downwardly along the central axis of the oil pressure sensor 3.

A decreased diameter portion 41, which is shaped such that an outer circumferential surface of the upper case 32 of the oil pressure sensor 3 can be tightly fitted therein, is arranged in an upper portion of the accommodation space 4. A horizontal section, that is, a section perpendicular to the axis of the oil pressure sensor 3, of the decreased diameter portion 41 is smaller than a horizontal section of a lower case 31 of the oil pressure sensor 3, and the lower case 31 cannot entirely enter into the decreased diameter portion 41. An increased diameter portion 42, in which an outer circumferential surface of the lower case 31, that is, a collar portion 7 of the lower case 31, is fitted, is arranged in a lower portion of the accommodation space 4. A shoulder portion 43 is defined at a boundary between the decreased diameter portion 41 and the increased diameter portion 42.

The oil pressure sensor 3 is a columnar member having a central axis extending in the vertical direction, and includes the lower case 31 and the upper case 32, which is fixed above the lower case 31. The lower case 31 and the upper case 32 correspond to a sensor case of the present invention. An outer circumference of the lower case 31 is arranged to project radially outward, i.e., in a horizontal direction in FIG. 2, beyond an outer circumference of the upper case 32 to assume the shape of a flange, and defines the collar portion 7.

An oil introducing space 34 is defined in the lower case 31. The oil introducing space 34 is arranged to open into the oil passage 21 at one end, and is closed at another end with a flexible plate 33 which is to be deformed in accordance with oil pressure. A groove 35, which is recessed upward from a lower surface of the lower case 31, is defined in the lower case 31. The groove 35 is arranged radially outside of the oil passage 21. A sealant 35a, such as, for example, an O-ring, is fitted in the groove 35. A surface of contact between the lower case 31 and the lower body 2 is sealed with the sealant 35a.

A pressure measuring space 36, which is arranged to surround an upper surface of the flexible plate 33, is defined in the upper case 32. A support member 37, a periphery of which is fixed to the upper case 32, is arranged in the pressure measuring space 36. A pressure sensor element 38 is arranged on a lower surface of the support member 37. The pressure sensor element 38 is arranged on an opposite side of the flexible plate 33 with respect to the oil introducing space 34. When the flexible plate is deformed by oil pressure from the oil passage 21, the pressure sensor element 38 detects a change in pressure by sensing a deformation of the flexible plate 33.

The upper case 32 is provided with terminal pins 39, each of which has spring-like elasticity and is connected to the pressure sensor element 38. An upper portion of the upper case 32 and the terminal pins 39 provided thereat are arranged to project from the accommodation space 4, which is defined in the upper body 1, and are exposed from the upper surface of the upper body 1.

At a surface of the upper case 32, the stoppers 50, which are two in number and each of which is arranged to project in a horizontal direction outwardly away from the central axis of the oil pressure sensor 3, are arranged at regular intervals, that is, at intervals of 180 degrees with the axis of the oil pressure sensor 3 as a center. Referring to FIG. 2, each stopper 50 is arranged at a level higher than that of a lower surface of the oil pressure sensor 3 by a thickness of the upper body 1. A lower surface of each stopper 50 is arranged at a level substantially the same as that of a lower surface of the upper case 32.

A distance from the central axis of the oil pressure sensor 3 to a projecting end of each stopper 50 is arranged to be smaller than a radius of the increased diameter portion 42 of the accommodation space 4, so that the stopper 50 can freely move in the vertical direction and in the circumferential direction within the increased diameter portion 42 without making contact with a wall surface of the increased diameter portion 42.

The distance from the central axis of the oil pressure sensor 3 to the projecting end of each stopper 50 is arranged to be greater than a radius of the decreased diameter portion 41. Accordingly, a wall surface of the decreased diameter portion 41 of the accommodation space 4 is provided with guide grooves 51 each of which is arranged to extend in the vertical direction, and the stoppers 50 are fitted into the guide grooves 51 such that the stoppers 50 are movable in the vertical direction. Each guide groove 51 is arranged to open into the increased diameter portion 42 of the accommodation space 4 at a lower end thereof, and is arranged to be open at the upper surface of the upper body 1 at an upper end thereof.

The upper body 1 includes the restricting portions 52, each of which is arranged to restrict a vertical movement of a corresponding one of the stoppers 50 in a situation in which the oil pressure sensor 3 is disposed in the accommodation space 4. In the present preferred embodiment, each restricting portion 52 is a portion of an upper edge of the accommodation space 4, the portion including no portion of any guide groove 51. A space portion, which is arranged to allow the stopper 50 to move therein when the oil pressure sensor 3 is rotated about the axis thereof extending in the vertical direction in the accommodation space 4, is arranged between each guide groove 51 and the corresponding restricting portion 52. The space portion, which allows the stopper 50 to move therein, is a portion of a space above the upper surface of the upper body 1, the portion adjoining the upper edge of the accommodation space 4 and being connected to an upper-end opening portion of the guide groove 51.

The first preferred embodiment, which has the above-described structure, has the following advantages.

When the oil pressure sensor 3 is attached to the upper body 1, the upper body 1 is turned upside down, and then, the oil pressure sensor 3, with the terminal pins 39 thereof taking the lead, is inserted into the accommodation space 4. At this time, the oil pressure sensor 3 is rotated about the axis thereof to allow the stoppers 50 to be fitted into the guide grooves 51 and to move along the guide grooves 51. Thus, the entire oil pressure sensor 3 can be inserted through the accommodation space 4, even with the stoppers 50 projecting outwardly relative to the wall surface of the decreased diameter portion 41.

Figure 3:
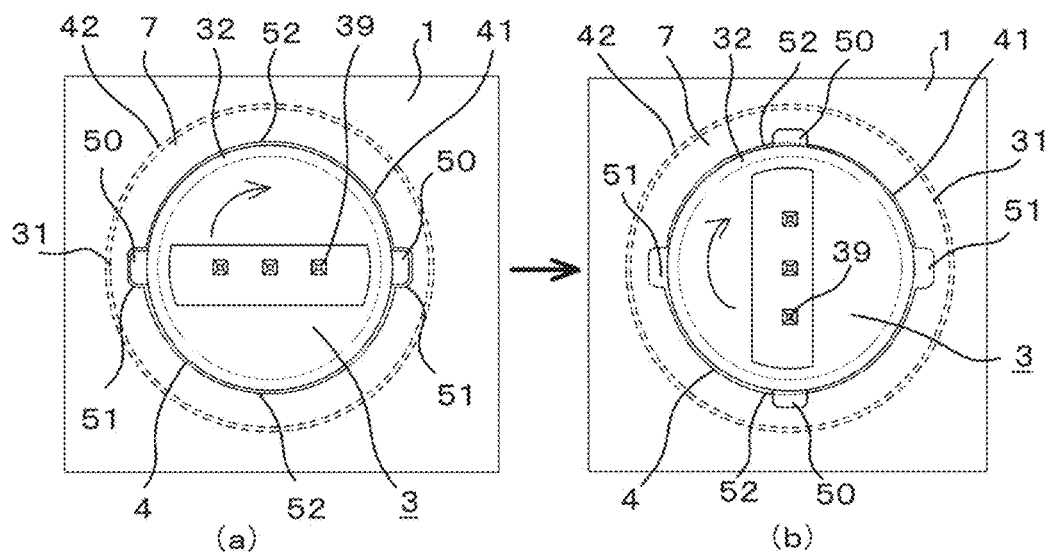
FIG. 3 is a plan view illustrating engagement between stoppers and restricting portions according to the first preferred embodiment.

When insertion of the oil pressure sensor 3 into the accommodation space 4 has been completed, the stoppers 50 have passed through the guide grooves 51 to be located above the upper body 1 as illustrated in (a) of FIG. 3. If the oil pressure sensor 3 is rotated about the axis thereof in this situation, each stopper 50 leaves the opening portion of the corresponding guide groove 51, and slides in the circumferential direction along the upper edge of the accommodation space 4. The stopper 50 is able to move in the circumferential direction at this time because the space portion, which allows the stopper 50 to move therein and which is connected to the opening portion of the guide groove 51, is provided at the upper surface of the upper body 1.

If each stopper 50 is rotated by 90 degrees as illustrated in (b) of FIG. 3, for example, the stopper 50 is engaged with the corresponding restricting portion 52, which is defined at the upper edge of the accommodation space 4, and is restrained from moving toward the lower body 2. At the same time, a portion of the upper case 32 is disposed in the decreased diameter portion 41 of the accommodation space 4, and a portion of the lower case 31 is disposed in the increased diameter portion 42, and thus, the oil pressure sensor 3 is held in the accommodation space 4 with a portion of the upper body 1 lying between the stoppers 50 and the shoulder portion 43.

After the oil pressure sensor 3 is temporarily fixed to the upper body 1 in the above-described manner, the upper body 1 is turned upside down, and is fitted on an upper surface of the lower body 2, and the upper and lower bodies 1 and 2 are fixed to each other. In this case, the oil pressure sensor 3 does not fall away from a lower surface of the upper body 1 because the oil pressure sensor 3 is temporarily fixed to the upper body 1.

After the upper and lower bodies 1 and 2 are fixed to each other, the collar portion 7 of the lower case 31 of the oil pressure sensor 3 is held between the shoulder portion 43 of the upper body 1 and a surface of the lower body 2. Accordingly, even if each stopper 50 is disengaged from the corresponding restricting portion 52, the oil pressure sensor 3 remains fixed between the upper body 1 and the lower body 2.

The following advantageous effects can be expected from the first preferred embodiment.

(1) Provision of the stoppers 50 and the restricting portions 52, which are arranged to hold the oil pressure sensor 3 in the accommodation space 4, prevents the oil pressure sensor 3 from falling off the upper body 1 in an operation stage before the oil pressure sensor 3 is fixed in a built-in manner between the upper and lower bodies 1 and 2 of a control valve. This contributes to preventing damage to the oil pressure sensor 3, and simplifying an assembling operation, and leads to improved productivity.

(2) Provision of projections as the stoppers 50 at the surface of the upper case 32 allows a simpler structure of the stoppers 50, a simpler structure of a mold for molding, and higher strength than in a case where the upper case 32 is provided with a stopper defined by an elastic member, and elasticity thereof is used to temporarily fix the oil pressure sensor 3 and the upper body 1 to each other.

(3) Since an edge of the accommodation space 4, which is an opening portion defined in the upper body 1, is used as each restricting portion 52, it is not particularly necessary to machine a wall surface of the accommodation space 4 or the like to form a protrusion or a recess therein when the accommodation space 4 is defined in the valve body.

(4) Since the collar portion 7 is arranged to extend over the entire circumferential extent of the lower case 31, the collar portion 7 has a large area, and can receive a pressing force of the upper body 1 with the large area. Thus, the lower case 31 can be securely fixed. In particular, the upper case 32 is made of a resin, and it is therefore easy to define the stoppers 50. The lower case 31, which is held between the upper and lower bodies 1 and 2, may be made of a metal having a high strength, and in this case, the oil pressure sensor 3 can be securely fixed by the upper and lower bodies 1 and 2.

2. Second Preferred Embodiment

Figure 4:
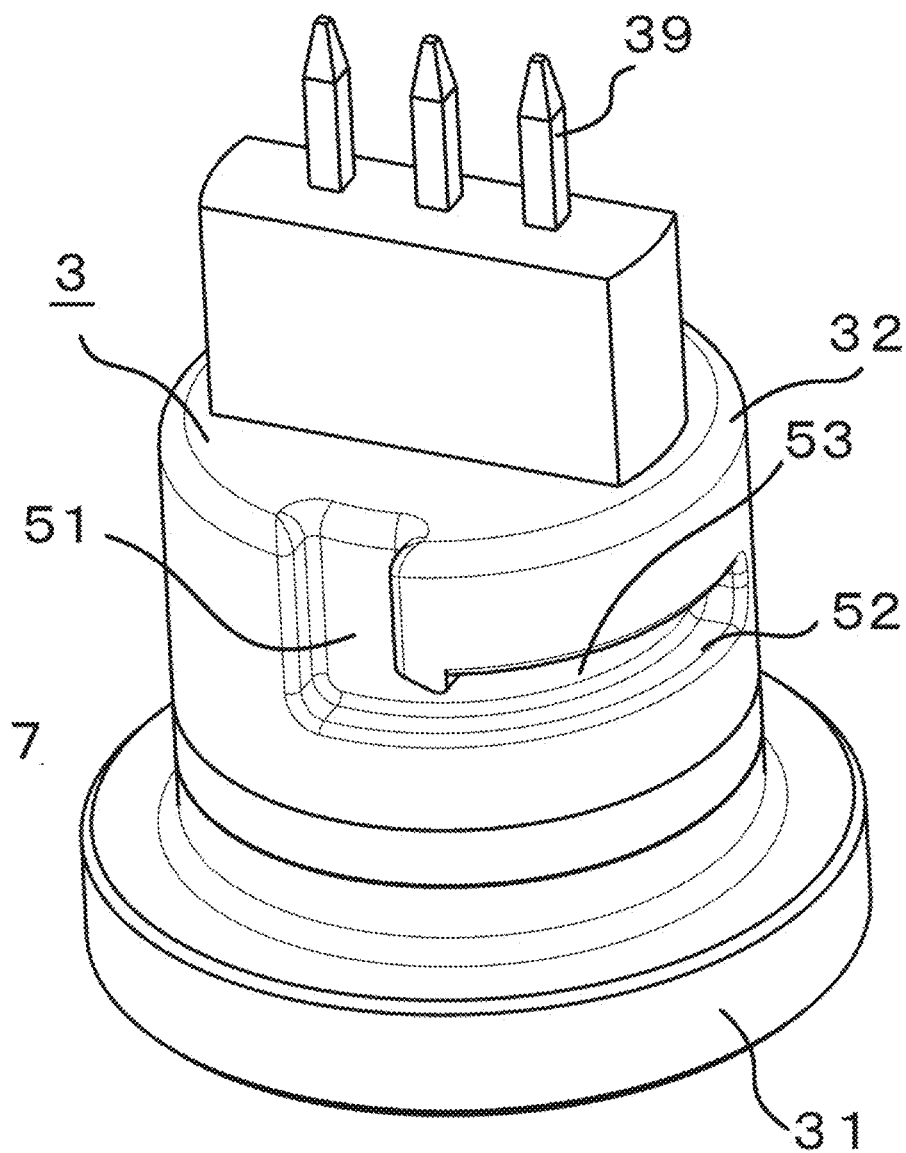
FIG. 4 is a perspective view of a second preferred embodiment of the present invention.
Figure 5:
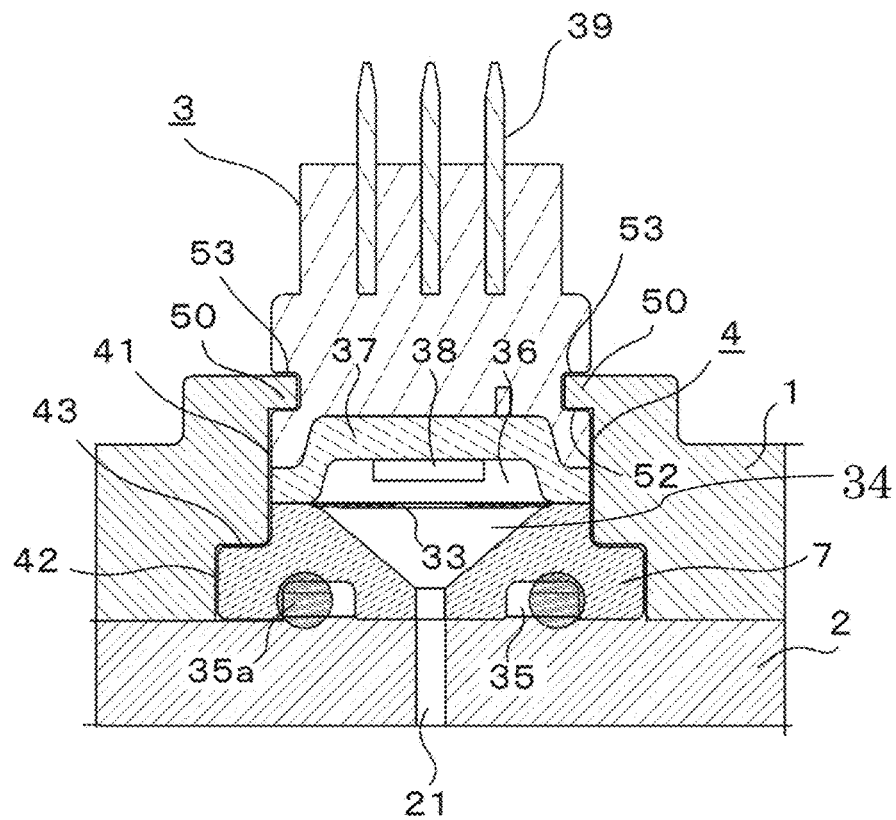
FIG. 5 is a vertical sectional view of the second preferred embodiment.

A second preferred embodiment of the present invention will now be described below with reference to FIGS. 4, 5, and 6. In a description of the second preferred embodiment, members or portions that have their equivalents in the first preferred embodiment are denoted by the same reference numerals as those of their equivalents in the first preferred embodiment, and descriptions of those members or portions are omitted. The second preferred embodiment is different from the first preferred embodiment in that stoppers 50 are included in an upper body 1, while guide grooves 51 and restricting portions 52 are included in an upper case 32 of an oil pressure sensor 3.

At an inner circumferential surface of an upper edge portion of an accommodation space 4, the stoppers 50, which are two in number and each of which is arranged to project in a horizontal direction toward an interior of the accommodation space 4, are arranged at regular intervals in the circumferential direction. Each guide groove 51 is arranged to extend in the vertical direction at an outer circumferential surface of the upper case 32, and a horizontal groove 53, which is connected to the guide groove 51 and is arranged to extend in the circumferential direction, is arranged at an upper-end opening portion of the guide groove 51. The stopper 50 is able to move in the guide groove 51 and the horizontal groove 53. A lower edge of the horizontal groove 53 defines the restricting portion 52, which is arranged to restrict a vertical movement of the stopper 50 in a situation in which the oil pressure sensor 3 has been inserted in the accommodation space 4. A space in the horizontal groove 53 defines a space portion allowing the stopper 50 to move therein between the guide groove 51 and the restricting portion 52.

The circumferential dimension of each horizontal groove 53 may be just large enough to allow the stopper 50 to be engaged with the restricting portion 52 of the horizontal groove 53, that is, approximately as large as a circumferential dimension of the stopper 50, for example. In the second preferred embodiment, however, the horizontal groove 53 is arranged to extend over an angular range of 90 degrees in the circumferential direction so that the oil pressure sensor 3 can be rotated by 90 degrees in the accommodation space 4.

Figure 6:
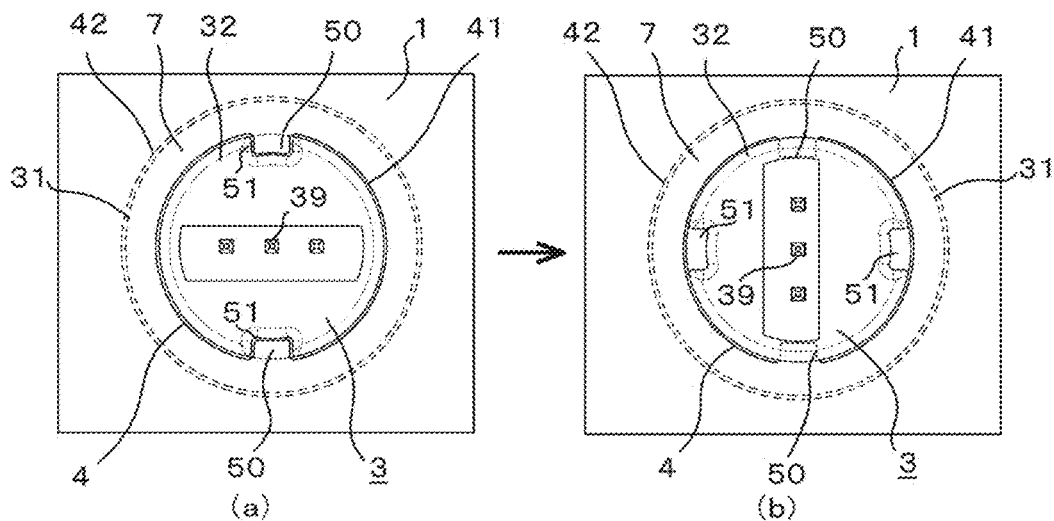
FIG. 6 is a plan view illustrating engagement between stoppers and restricting portions according to the second preferred embodiment.

In the second preferred embodiment, as illustrated in (a) of FIG. 6, the oil pressure sensor 3 is inserted into the accommodation space 4 with the stoppers 50 entering into the guide grooves 51. If the oil pressure sensor 3 is rotated by 90 degrees in the accommodation space 4 in a situation in which each stopper 50 has reached an upper end of the corresponding guide groove 51, the stopper 50 enters into the corresponding horizontal groove 53. Then, if the stopper 50 reaches an end portion of the horizontal groove 53, the stopper 50 is engaged with the corresponding restricting portion 52 as illustrated in (b) of FIG. 6 to prevent the oil pressure sensor 3 from falling off the upper body 1. Thus, advantageous effects similar to those of the first preferred embodiment can be achieved.

In the second preferred embodiment, the guide grooves 51 and the horizontal grooves 53 are defined in the upper case 32, which is made of a resin. Therefore, it is possible to define the guide grooves 51 and the horizontal grooves 53 at one time by a resin molding process using a mold, which allows easier manufacture than in the case where the upper body 1 is made of a metal and the guide grooves 51 are defined in the upper body 1 made of the metal.

3. Other Preferred Embodiments

The present invention is not limited to the above-described preferred embodiments. The above-described preferred embodiments have been presented by way of example only, and the present invention can be embodied in a variety of other forms. Various omissions, substitutions, and changes may be made without departing from the scope of the invention. These preferred embodiments and modifications thereof fall within the scope and spirit of the invention and the scope of equivalents thereof. Examples thereof will now be described below.

Figure 7:
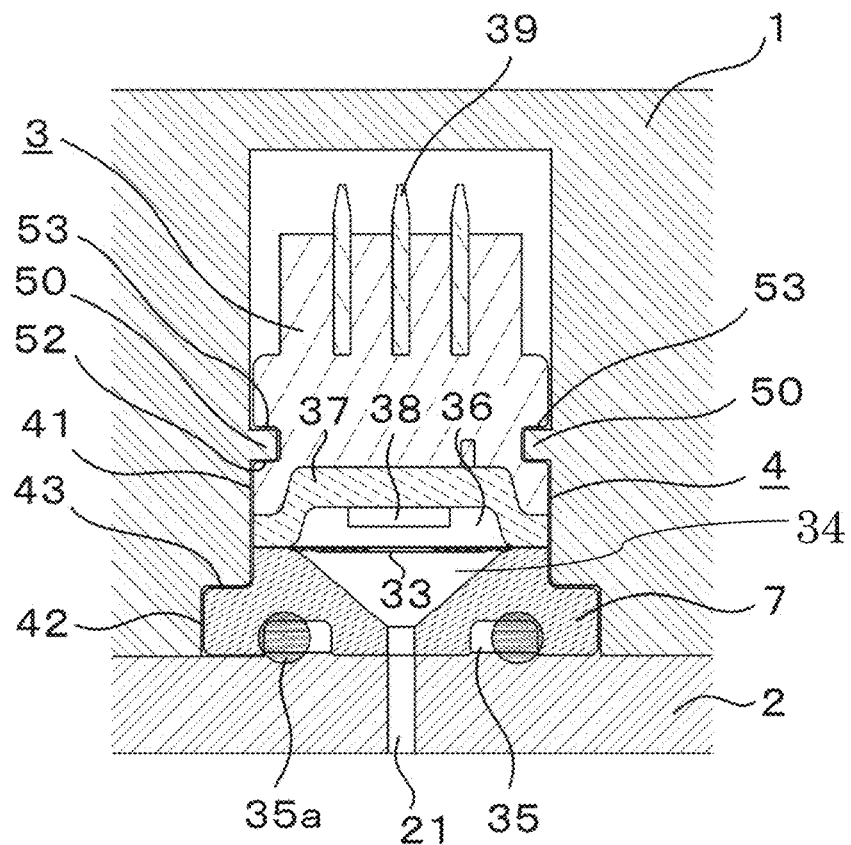
FIG. 7 is a vertical sectional view of a modification of the second preferred embodiment.

(1) A low-profile, so-called button-type oil pressure sensor may be used as a columnar sensor having a central axis in a preferred embodiment of the present invention. In this case, an accommodation space 4 may be a recessed portion defined in a lower surface of an upper body 1 as illustrated in FIG. 7. In FIG. 7, stoppers 50 are included in the upper body 1. Note, however, that, in the case where the accommodation space 4 is the recessed portion, the stoppers 50 may alternatively be defined in an outer circumference of a sensor case, while guide grooves 51 and horizontal grooves 53 may be defined in a wall surface of the accommodation space 4, with a lower edge of each horizontal groove 53 defining a restricting portion 52.

(2) The number of stoppers 50 included in the sensor case or the upper body 1 is not limited to two, but may be more than two, as long as the stoppers 50 are arranged at regular intervals in the circumferential direction. The number of stoppers may be one as long as the one stopper is so shaped as to be capable of securely fixing the sensor case to the upper body 1.

(3) Each stopper 50 may alternatively be defined by a member separate from the case of the oil pressure sensor 3 and the upper body 1, and may be fixed to the sensor case or the upper body 1 through, for example, screwing, fitting, or adhesion.

(4) The structure of the oil pressure sensor 3 is not limited to those of the preferred embodiments illustrated in the figures. Each stopper may be defined in the lower case 31, the support member 37, or another portion of a body portion of the oil pressure sensor, instead of in the upper case 32 as in the first preferred embodiment.

(5) Materials of the upper case 32 and the lower case 31 are not limited to those of the preferred embodiments illustrated in the figures. The upper case 32 may be made of, for example, a metal instead of a resin, as long as the stopper 50 can be defined in the upper case 32. The lower case 31 may alternatively be made of a resin.

(6) The collar portion 7, which is defined in the lower case 31, does not need to be in the shape of a flange extending over the entire circumferential extent of the lower case 31. Projecting portions may be defined at the outer circumference of the lower case 31 at regular intervals or at appropriate intervals, and upper surfaces of the projecting portions may be used as the collar portion 7.

Features of the above-described preferred embodiments and the modifications thereof may be combined appropriately as long as no conflict arises.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A sensor attachment structure comprising:
   an oil pressure sensor including a sensor case and a pressure sensor element accommodated in the sensor case, the sensor case including a body portion having a circular horizontal section; and
   a valve body including an upper body and a lower body, the upper body including an accommodation space having a wall surface having a circular horizontal section, the accommodation space having the body portion inserted therein such that the body portion is capable of rotating about a central axis thereof extending in a vertical direction, the lower body including an oil passage arranged to extend therethrough toward the upper body; wherein
   the upper body includes a stopper arranged to project in a horizontal direction toward an interior of the accommodation space at the wall surface of the accommodation space;
   an outer circumferential surface of the body portion includes a guide groove arranged to extend in the vertical direction and allow the stopper to move therein;
   the outer circumferential surface of the body portion includes a restricting portion arranged to restrict a vertical movement of the stopper in a situation in which the body portion has been inserted in the accommodation space; and
   a space portion allowing the stopper to move therein is arranged between the guide groove and the restricting portion.

2. The sensor attachment structure according to claim 1, wherein
   the space portion is a horizontal groove arranged to extend in a circumferential direction at the outer circumferential surface of the body portion, the horizontal groove being connected to the guide groove extending in the vertical direction; and
   the restricting portion is defined by a lower edge of the horizontal groove.

3. The sensor attachment structure according to claim 1, wherein
   the sensor case includes a lower case and an upper case fixed above the lower case;
   the upper case is made of a resin, and is arranged to have the pressure sensor element disposed inside thereof; and
   the lower case is made of a metal, has arranged inside thereof an oil introducing space connected to the oil passage defined in the lower body, includes a collar portion at an outer circumference thereof, and is held with the collar portion being held between the upper body and the lower body.

* * * * *